United States Patent [19]

Bartels

[11] Patent Number: 4,847,391
[45] Date of Patent: Jul. 11, 1989

[54] PROCESS FOR PREPARING 2-(3-BROMOPROPYL)-5,5-DIMETHYL-1,3-DIOXANE AND 2-(4-BROMOBUTYL-5,5-DIMETHYL-1,3-DIOXANE

[76] Inventor: Günter Bartels, c/o Hoechst Aktiengesellschaft, P.O. Box 80 03 20, D-6230 Frankfurt am Main 80, Fed. Rep. of Germany

[21] Appl. No.: 919,837

[22] Filed: Oct. 16, 1986

[30] Foreign Application Priority Data

Oct. 19, 1985 [DE] Fed. Rep. of Germany ....... 3537289

[51] Int. Cl.$^4$ .......................................... C07D 319/06
[52] U.S. Cl. ................................ 549/369; 549/374
[58] Field of Search .............................. 549/374, 369

[56] References Cited

U.S. PATENT DOCUMENTS 4,252,803 2/1981 Webb .............................. 544/80 Z

OTHER PUBLICATIONS

Sandler et al., "Organic Functional Group Preparations", Academic Press, New York, 1968, pp. 116–123.
Forbes, C. et al., J. Chem. Soc., Perkin I (1977), 2353–2355.
Kuehne, M. et al., J. Org. Chem., 46, 2002–2009 (1981).
Little, R. D. et al., J. Org. Chem., 47, 362–364 (1982).
Kulkarni, S. et al., Heterocycles, 18, 163–167 (1982).
Fleming, I. et al., Snyth. Commun., 5, 177–180 (1975).
Meerwein, H., "Preparations of Acetals", in Houben-Weyl, Meth. der Org. Chem., vol. VI(3), (1965), pp. 204–215.
Roedig, A., "Prep. of Bromine Compounds", in Houben-Weyl, Meth. der Org. Chem., vol. V(4) (1960), pp. 361–380.

Primary Examiner—Nicky Chan

[57] ABSTRACT

The invention relates to a process for preparing the ketals of 4-bromobutanal and of 5-bromopentanal of the formula

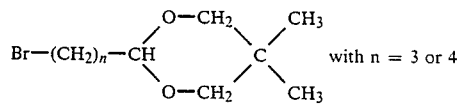

which comprises reacting 2,3-dihydroguran and 3,4-dihydro-2H-pyran respectively in a solvent in the presence of a catalyst with neopentylglycol and then brominating the resulting product. The invention also relates to the said ketal of 5-bromobutanal as such.

5 Claims, No Drawings

PROCESS FOR PREPARING 2-(3-BROMOPROPYL)-5,5-DIMETHYL-1,3-DIOXANE AND 2-(4-BROMOBUTYL-5,5-DIMETHYL-1,3-DIOXANE

The invention relates to a process for preparing the ketals of 4-bromobutanal and of 5-bromopentanal of the formula I

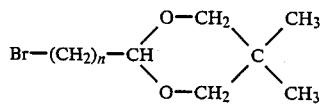  (I)

in which n is 3 or 4, and to the latter compound as such. The compounds of the formula I are ketalized ω-halogenoalkanals, hereinafter also referred to in brief as "halogenoketals", whose basic structure can be described by means of the formula II:

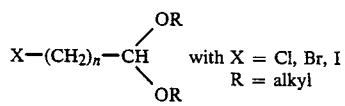  (II)

Halogenoketals of the general structure II with n=3 or 4 are described in the literature. They are useful bifunctional intermediates which can be made to react on the one hand in the customary reactions of an alkyl halide and on the other hand, after cleavage of the ketal function, in the many possible reactions of an aldehyde. Such compounds are used for example in the synthesis of alkaloids (C. P. Fobes et al., J. Chem. Soc. Perkin I (1977), page 2353; M. E. Kuehne et al., J. Org. Chem. 1981, volume 46, page 2002) and indole derivatives (U.S. Pat. No. 4,252,803).

Bromoketals of the formula II with X=Br and n=3 or 4 have hitherto been prepared by reacting 4-bromobutanal or 5-bromopentanal of the formula III Br—(CH₂)ₙ—CHO with n=3,4  (III)

with appropriate alcohols or diols.

However, the 4-bromobutanal or 5-bromopentanal required for this reaction is not available on an industrial scale. The following methods for preparing these two compounds are known:

1. Partial reduction of 4-bromobutyronitrile or 5-bromovaleronitrile to 4-bromobutanal and 5-bromopentanal respectively with diisobutylaluminum hydride (R. D. Little, J. Org. Chem. 1982, 47, Pages 362–364).
2. Oxidation of the corresponding halogenoalcohols with pyridinium chlorochromate (S. U. Kulkarni, Heterocycles 1982, 18, pages 163–167).

The reagents used herein, however, are not suitable for industrial processes. For that reason the bromoketals of the formula I have hitherto not been preparable on an industrial scale.

It has now been found, surprisingly, that these bromoketals can be prepared by a simple conversion from the cyclic compounds 2,3-dihydrofuran (IV) and 3,4-dihydro-2H-pyran (V).

  IV

  V respectively. To this end, these two compounds are first reacted with neopentylglycol:

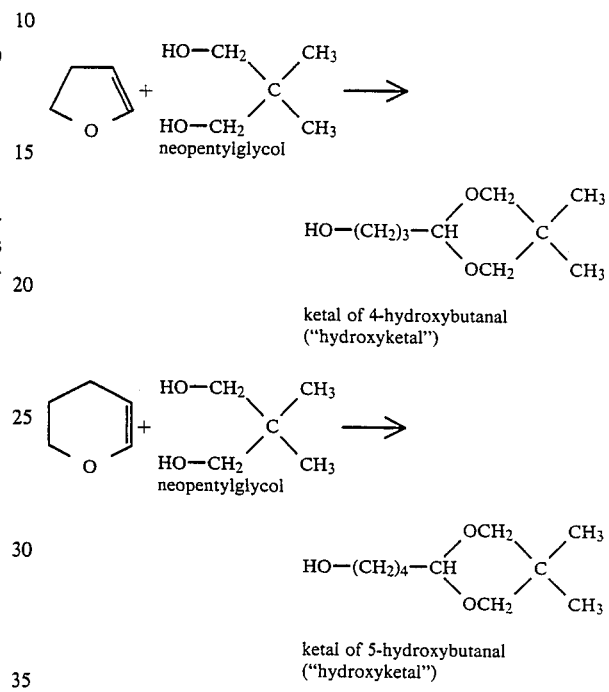

The resultng hydroxyketals are then converted into the bromoketals.

Said reaction of the dihydropyran V to give the corresponding hydroxyketal is already known from the literature (Synth. Communications 5 (1975), pages 177–180). To prepare the corresponding bromoketal, however, there the hydroxyketal is first converted with p-toluenesulfonyl chloride and triethylamine into the corresponding tosylate, which forms in the course of 10 days in a yield of only 50%. The tosylate is then converted with lithium bromide into the bromoketal I (with n=4), the yield being only 44%. Based on starting dihydropyran V, the yield of bromoketal I (with n=4) is therefore merely 22%. In the present process, the yield for this compound is over 60%.

The process according to the invention for preparing the ketals of 4-bromobutanal and of 5-bromopentanal of the formula

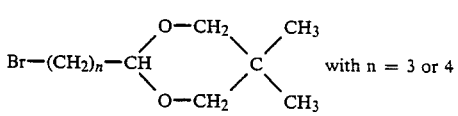 with n = 3 or 4 comprises reacting 2,3-dihydrofuran and 3,4-dihydro-2H-pyran respectively in a solvent in the presence of a catalyst with neopentylglycol and then brominating the resulting product.

Preferably, approximately equimolar amounts of neopentylglycol are used. Suitable catalysts are all compounds which are customarily used in the conversion of aldehydes into ketals (see Houben-Weyl, Methoden der Organischen Chemie [Methods of organic chemistry], volume VI/3 (1965), page 204 et seq., in particular page 215), for example hydrochloric acid, sulfuric acid, sulfonic acids, sodium hydrogensulfate, phosphoric acid, phosphorous pentoxide, iron(III) chlorie, zinc chloride, iodine, anhydrous copper(II) sulfate. Preferred catalysts are sulfonic acids, in particular p-toluenesulfonic acid. Suitable solvents are all nonprotic solvents which guarantee adequate solubility of the reactants. Preferred solvents are chlorinated hydrocarbons and aromatic hydrocarbons or corresponding solvent mixtures, in particular 1,2-dichloroethane, methylene chloride and toluene. In particularly preferred embodiment, the neopentylglycol is introduced first, together with catalytic amounts of p-toluenesulfonic acid, in 1,2-dichloroethane, and dihydrofuran (IV) and dihydropyran (V) respectively are added dropwise at 0° to 20° C. with cooling. The reaction is then allowed to proceed to completion at a temperature between 20° C. and the boiling point of the solvent.

The hydroxyketals formed as intermediates can be isolated out of the reaction solution, after neutralization, by distillation. However, preferably they are reacted further in the reaction solution, i.e. without isolation, with a brominating agent. Suitable brominating reagents are all compounds which are customarily used for converting alcohols into alkyl bromides and guarantee the preservation of the ketal function (see Houben-Weyl, volume V/4 (1960), page 361 et seq.). These include, for example, phosphorus bromides and SOBr$_2$. When phosphorus tribromide is used, then, in accordance with a known procedure (see Houben-Weyl, volume V/4 (1960), pages 379, 380), the phosphorus bromide is first introduced dropwise at 0°–10° C. with cooling and subsequently heated to the boiling point of the solvent until completion of the reaction. The crude product obtained following conventional working up (Houben-Weyl, V/4 (1960), pages 379, 380) is purified by distillation in vacuo. The bromoketals are obtained in a yield of 60-70%.

EXAMPLE 1

2-(4-Bromobutyl)-5,5-dimethyl-1,3-dioxane (=I with n=4)

To a suspension of 833 g of neopentylglycol in 2.5 liters of 1,3-dichloroethane were added dropwise at room temperature and after addition of 8 g of p-toluenesulfonic acid 673 g of 3,4-dihydro-2H-pyran in the course of 60 minutes. A reaction time of 16 hours at room temperature was followed by cooling down to 0° C. and the dropwise addition in the course of 1.5 hours of 758 g of phosphorus tribromide. The reaction was left at 0° C. for 3 hours and 80° C. for 3 hours. The reaction solution, after cooling down to room temperature, was washed with water and carbonate solution and evaporated. The crude product gave on distillation in a high vacuum 1250 g of product (62% of theory) in a purity of 94% (GC).

EXAMPLE 2

2-(3-Bromopropyl)-5,5-dimethyl-1,3-dioxane (=I with n=3)

To a suspension of 833 g of neopentylglycol in 2.5 liters of 1,2-dichloroethane were added dropwise at room temperature and after addition of 8 g of p-toluenesulfonic acid 561 g of 2,3-dihydrofuran in the course of 60 minutes. A reaction time of 16 hours at room temperature was followed by cooling down to 0° C. and the dropwise addition in the course of 1.5 hours of 758 g of phosphorus tribromide. The reaction was left at 0° C. for 3 hours and 80° C. for 3 hours. The reaction solution, after cooling down to room temperature, was washed with water and carbonate solution and evaporated. The crude product gave on distillation in a high vacuum 1270 g of product (67% of theory) in a purity of 93% (GC). Boiling point 79° C. at 0.13 mbar NMR spectrum (CDCl$_3$):

0.72 ppm (s) 3H 1.17 ppm (s) 3H 1.4–2.3 ppm (m) 4H 3.2–3.8 ppm (m) 6H 4.44 ppm (t, 5 Hz) 1H

I claim:

1. A process for preparing the ketals of 4-bromobutanal and of 5-bromopentanal of the formula

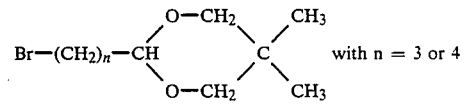

which comprises reacting 2,3-dihydrofuran and 3,4-dihydro-2H-pyran respectively in a solvent in the presence of a catalyst with neopentylglycol and then brominating the resulting product.

2. The process as claimed in claim 1, wherein approximately equimolar amounts of neopentylglycol are used.

3. The process as claimed in claim 1, wherein the catalyst used is a sulfonic acid.

4. The process as claimed in claim 1, wherein the bromination is effected with a phosphorus bromide or SOBr$_2$.

5. The process as claimed in claim 1, wherein n is 3, wherein 2,3-dihydrofuran is reacted with neopentylglycol to obtain the ketal of 4-hydroxybutanal as an intermediate, and the said intermediate is brominated with a phosphorus bromide or SOBr$_2$ to obtain 2-(3-bromopropyl)-5,5-dimethyl-1,3-dioxane.

* * * * *

UNITED STATES PATENT AND TRADEMARK OFFICE
CERTIFICATE OF CORRECTION

PATENT NO. : 4,847,391
DATED : July 11, 1989
INVENTOR(S) : Gunter Bartels

It is certified that error appears in the above-identified patent and that said Letters Patent is hereby corrected as shown below:

In column 3, line 46: "1,3-dichloroethane" should read --1,2-dichloroethane--.

Signed and Sealed this

Second Day of October, 1990

Attest:

HARRY F. MANBECK. JR.

Attesting Officer

Commissioner of Patents and Trademarks